United States Patent [19]

Malamas et al.

[11] Patent Number: 5,541,205
[45] Date of Patent: Jul. 30, 1996

[54] ARYL-N-HYDROXYUREAS AS INHBITORS OF 5-LIPOXYGENASE AND ANTI-ARTERIOSCLEROTIC AGENTS

[75] Inventors: Michael S. Malamas, Jamison, Pa.; Iwan Gunawan, Somerset, N.J.

[73] Assignee: American Home Products Corporation, Madison, N.J.

[21] Appl. No.: 409,781

[22] Filed: Mar. 24, 1995

Related U.S. Application Data

[62] Division of Ser. No. 148,602, Nov. 8, 1993, Pat. No. 5,428,048.

[51] Int. Cl.$^6$ .................. A61K 31/415; A61K 31/42; A61K 31/425
[52] U.S. Cl. .................. 514/364; 514/365; 514/374; 514/375
[58] Field of Search .................. 514/364, 365, 514/374, 375

[56] References Cited

U.S. PATENT DOCUMENTS 5,428,048  6/1995  Malamas et al. .................. 514/364

FOREIGN PATENT DOCUMENTS

| 0279281 | 2/1988 | European Pat. Off. . |
| 0384594 | 8/1988 | European Pat. Off. . |
| 9012008 | 10/1990 | WIPO . |
| 9203130 | 3/1992 | WIPO . |
| 9203425 | 3/1992 | WIPO . |

OTHER PUBLICATIONS

Reaven et al. Arteriosclerosis & Thrombosis 12(3) 318–21 1992.
Steinberg, Amer. J. of Cardiology 57, 16H–21H 1986.
Carew et al., Proc. Natl. Acad. Sci. 84 7725–29 1987.
Nagano et al., Arteriosclerosis 9(4) 453–461 1989.
Moskowitz, Medline Abs. #91080793, 1991.

*Primary Examiner*—Richard L. Raymond
*Assistant Examiner*—Mary Cebulak
*Attorney, Agent, or Firm*—R. F. Boswell, Jr.

[57] ABSTRACT

This invention relates to compounds which inhibit lipoxygenase in the metabolism of arachidonic acid and thus inhibits formation of leukotrienes which are implicated in inflammatory processes and bronchoconstriction and inhibits the oxidation of LDL which is implicated in formation of atherosclerotic plaque.

The compounds useful in this invention are represented by the formula:

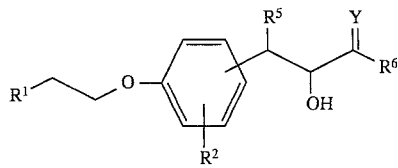

wherein: $R^2$ is hydrogen, halogen or $C_1$–$C_6$ alkyl; Y of O or S; $R^5$ is hydrogen or methyl
$R^6$ is —$NH_2$, —$CH_3$ or —$OCH_3$;
and $R^1$ is

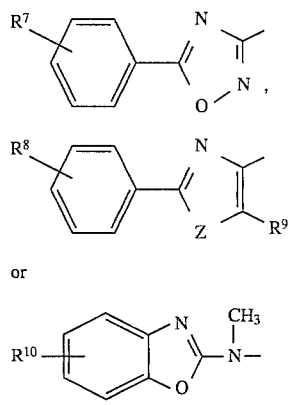

wherein $R^7$, $R^8$ and $R^{10}$ are independently halogen, trifluoromethyl, alkyl, alkoxy, methanesulfonyl or trifluoromethanesulfonyl; $R^9$ is hydrogen or methyl; and Z is O or S,
or a pharmaceutically acceptable salt thereof.

2 Claims, No Drawings

15,541,205

ARYL-N-HYDROXYUREAS AS INHBITORS OF 5-LIPOXYGENASE AND ANTI-ARTERIOSCLEROTIC AGENTS

This is a division of application Ser. No. 08/148,602, filed Nov. 8, 1993, now U.S. Pat. No. 5,428,048.

This invention relates to aryl-N-hydroxyureas which have 5-lipoxygenase inhibition properties, a method for inhibiting the biosynthesis of leukotrienes and pharmaceutical compositions for inhibiting leukotriene synthesis and are thus useful as antiinflammatory and anti-asthma agents. Compounds of this invention also have the ability to scavenge peroxyl radicals implicated in the oxidation of low density-lipoprotein and thus are useful in the treatment of conditions for which the inhibition of oxidative modification of lipids is indicated such as atherosclerosis.

BACKGROUND OF THE INVENTION

Leukotrienes participate in inflammatory reactions, exhibit chemotactic activities, stimulate lysosomal enzyme release and act as important factors in the intermediate hypersensitivity reaction. Leukotrienes are metabolic products of metabolism of arachidonic acid (AA) by lipoxygenase enzymes with the most significant leukotrienes being $LTB_4$, $LTC_4$, $LTD_4$ and $LTE_4$. The latter three leukotrienes are incorporated in the substance known as SRS or SRS-A, the slow-reacting substance of anaphylaxis [*J. Immun.* 215, 115–118 (1980), *Biochem. Biophys. Res. Comm.* 93, 1121–1126(1980)]. By another metabolic pathway, arachidonic acid is metabolized by cyclooxygenase enzymes to prostaglandins and thromboxanes.

Leukotrienes $LTC_4$ and $LTD_4$ are potent bronchoconstrictors of the human bronchi [Dahlen et al., *Nature* 288, 484–486 (1980) and Piper, *Int. Arch. Appl. Immunology* 76, Suppl. 1, 43 (1985)] which stimulate the release of mucus from airways in vitro [Macom et al., *Am. Rev. Resp. Dis.* 126, 449 (1982)], are potent vasodilators in skin [Bisgaard et al., *Prostaglandins* 23, 797 (1982)], and produce a wheal and flare response [Camp et al., *Brit. J. Pharmacol.* 80 497 (1983)]. The nonpeptide leukotriene LTB4 is a powerful chemotactic factor for leukocytes [A. S. Ford—Hutchinson, *J. Royal Soc. Med.* 74, 831–883 (1981)], which stimulates cell accumulation and affects vascular smooth muscle [Bray, *Brit. Med. Bull.* 39, 249 (1983)]. The activity of leukotrienes as mediators of inflammation and hypersensitivity is extensively reviewed [Bailey and Casey, *Ann. Reports Med. Chem.* 17, 203–217 (1982) and Bray, *Agents and Actions* 19, 87 (1986) and Masamune and Melvin, *Ann. Reports Med. Chem.* 24, 71 (1989)].

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, *Gastroenterology,* 77, 761–767 (1979)] and this action of the prostaglandins, especially of the E series, is considered to be of importance in the treatment of gastrointestinal ulceration [see Isselbacher, *Drugs,* 33 (suppl.), 38–46 (1987)]. On the other hand, ex vivo experiments have shown that gastric mucosal tissue from ethanol-pretreated rats is capable of $LTC_4$ generation and that this $LTC_4$ production is quantitatively related to the severity of the ethanol damage [see Lange et at., *Naunyn-Schmiedeberg's Arch. Pharmacol. Suppl.,* 330, R27, (1985)]. It has also been demonstrated that $LTC_4$ can induce vasoconstriction in both venous and arteriolar vessels in the rat submucosa [see Whittle, *JUPHAR Ninth Int. Cong. of Pharmac.,* S30–2, London, England (1984)]. This is significant since ethanol-induced lesion formation in gastric mucosa may be multifactorial with, for example, stasis of gastric blood flow contributing significantly to the development of the hemorrhagic necrotic aspects of the tissue injury [see Guth et al., *Gastroenterology,* 87, 1083–90 (1984)]. Moreover, in the anesthetized cat, exogenous $LTD_4$ evokes both increased pepsin secretion and decreased transgastric potential [Pendleton et al., *Eur. J. Pharmacol.,* 125, 297–99 (1986)]. A particularly significant recent finding in this regard is that 5-lipoxygenase inhibitors and some leukotriene antagonists protect the gastric mucosa against lesions induced by the oral or parenteral administration of most nonsteroidal antiinflammatory drugs [see Rainsford, *Agents and Actions,* 21, 316–19 (1987)]. Accordingly, a significant body of evidence implicates the involvement of lipoxygenase products in the development of pathological features associated with gastric mucosal lesions, such as for example those induced by ethanol exposure and administration of non-steroidal anti-inflammatory drugs. Thus, compounds which inhibit the biological effects of leukotrienes and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to tile metabolism of AA to leukotrienes, indicates that a rational approach to drug therapy to prevent, remove or ameliorate the symptoms of allergies, anaphylaxis, asthma and inflammation and for gastric cytoprotection must focus on either blocking tile release of mediators of these conditions or antagonizing their effects. Thus compounds, which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions and in providing gastric cytoprotection.

Compounds of this invention inhibit lipoxygenase and antagonize products of the lipoxygenase pathway and thus are useful as antiinflammatory and anti-allergic agents. Compounds of this invention are expected to have gastric cytoprotective activity.

Atherosclerosis, the underlying disease implicated in myocardial infarction and strokes, is a complex pathologic process involving the intimal layer of the arteries. The earliest lesion of atherosclerosis is development of the fatty streak lesions which contain lipid-laden macrophages and lipid-laden smooth muscle cells. Macrophages do not take up native low density lipoprotein (LDL) but do take up modified, i.e., acetylated LDL or oxidized LDL via acetyl-LDL or "scavenger" receptors to form the foam cells of atherosclerotic plaque. Free radial oxidation, i.e., lipid peroxidation, has been shown to be involved in the alteration of LDL by endothelial cells. Arterial smooth muscle cells generate superoxide and oxidize LDL in the presence of micromolar concentrations of $Cu^{+2}$ or $Fe^{+2}$. The way LDL can be modified by endothelial cells can be mimicked in vitro by incubation of the lipoprotein in the presence of $CuCl_2$. Probucol, an antihyperlipidemic agent, also inhibits both cell mediated and $Cu^{+2}$ mediated oxidative modification of LDL, and was shown to inhibit the formation of atherosclerotic lesions in WHHL rabbits [Reaven et al., *Arteriosclerosis and Thrombosis* 12(3), 318–324 (1992), Steinberg, *The Amer. J. of Cardiology* 57, 16H–21H (1986), Carew. Schwenke and Steinberg, *Proc. Natl. Acad. Sci.* 84, 7725–7729 (1987) and Nagano et al., *Arteriosclerosis* 9 (4), 453–461 (1989)]. Thus in vitro inhibition of $Cu^{+2}$ catalyzed oxidation of LDL is indicative of antiatherosclerotic utility.

Compounds of this invention inhibit in vitro the copper-induced peroxidation of LDL and thus would be useful in the treatment or prevention of arteriosclerosis.

Lipoxygenase inhibiting compounds of the formula:

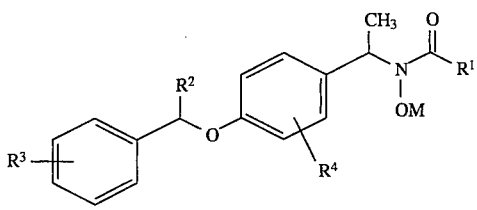

wherein $R^1$ is amino or methyl, $R^2$ is $C_1$–$C_2$ alkyl, $R^3$ is selected from hydrogen, halogen, and trihalomethyl; $R^4$ is hydrogen, halogen, trihalomethyl, $C_1$–$C_4$ alkoxy or $C_1$–$C_4$ alkyl; and M is hydrogen, a pharmaceutically acceptable cation, aroyl or $C_1$–$C_6$ alkoyl are disclosed in EP 0279281 A2. EP 0384594 A1 discloses antiinflammatory 5-lipoxygenase inhibitors of the formula:

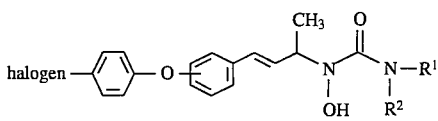

wherein $R^1$ and $R^2$ are selected from H and $C_1$–$C_4$ alkyl independently and the 4-halophenoxy moiety can be attached to the phenyl ring at either the 3 or 4 position.

The PCT patent WO 90/12008 discloses lipoxygenase inhibiting compounds of the formula:

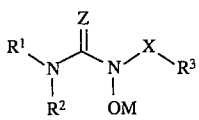

wherein M is, among other choices, hydrogen or a pharmaceutically acceptable cation; Z is O or S; X is a straight or branched $C_1$–$C_6$ alkylene or $C_2$–$C_6$ alkenylene group optionally substituted by hydroxy, halogen, cyano, alkoxy, aminocarbonyl, carboxy and alkoxycarbonyl; $R^1$ and $R^2$ are independently hydrogen, hydroxy, or $C_1$–$C_6$ alkyl optionally substituted by hydroxy, halogen, cyano, alkoxy, etc., with a proviso that both $R^1$ and $R_2$ cannot hydroxy; and $R_3$ can be phenyl, naphthyl or thienyl optionally substituted by a variety of substituents including carbocyclic or heterocyclic arylalkoxy groups optionally substituted by halogen, nitro, cyano, alkyl, alkoxy or halosubstituted alkyl wherein the heterocyclic aryl moiety is defined as a 5 to 6 membered ring containing one N, S, or O atom or a N and O or a N and S or three N atoms and further stipulates that the 5 to 6 membered heterocyclic aryl moiety may be fused with a phenyl ring to form a benzo-fused heterocycle. The PCT application WO 92/03425 discloses compounds that are intermediates to antidiabetic compounds having the formula:

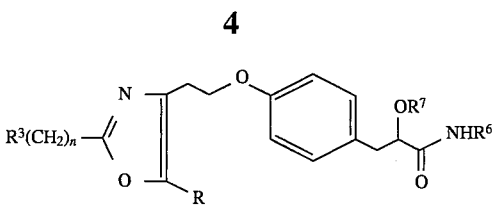

wherein n is 0 or 1, R is hydrogen or $C_1$–$C_3$ alkyl, $R^3$ is one of $C_1$–$C_9$ alkyl, $C_3$–$C_7$ cycloalkyl, phenyl, naphthyl, furyl, benzofuryl or thienyl optionally substituted with one or two groups selected from $C_1$–$C_3$ alkyl, $C_1$–$C_3$ alkoxy, $C_1$–$C_3$ alkoxycarbonyl, trifluoromethyl, fluoro or chloro; $R^6$ is hydrogen, $C_1$–$C_9$ alkyl, $C_3$–$C_7$ cycloalkyl, phenyl, naphthyl, furyl, benzofuryl or thienyl and $R^7$ is hydrogen or a conventional protecting group. N-Aryl-N-hydroxy ureas, formamides and alkylamides having previously been disclosed to have lipoxygenase inhibiting activity, are disclosed in WO 92/03130 as having anti-atherosclerotic activity and have the formula:

Ar—Y—Q wherein Ar is heteroaromatic, naphthyl, tetrahydronaphthyl, phenyl or phenyl substituted by phenyl, naphthyl or a heteroaromatic group; Y is $C_1$–$C_{10}$ alkylene or $C_2$–$C_{10}$ alkylene and Q is

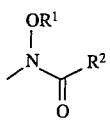

where $R^1$ is H, $C_1$–$C_4$ alkyl or an Ar group and $R^2$ is H, $C_1$–$C_4$ alkyl, amino, mono or dialkylamino, cycloalkylamino, cycloalkylalkylamino, anilino, N-alkylanilino or an Ar group.

SUMMARY OF THE INVENTION

The compounds useful in the methods and pharmaceutical compositions of this invention are represented by Formula I:

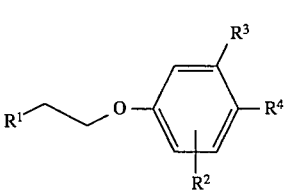

wherein:

$R^2$ is hydrogen, halogen or $C_1$–$C_6$ alkyl;

one of $R^3$ and $R^4$ is H and the other is

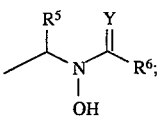

Y is O or S;

$R^5$ is hydrogen or methyl;

$R^6$ is —$NH_2$, —$CH_3$ or —$OCH_3$;

and R¹ is

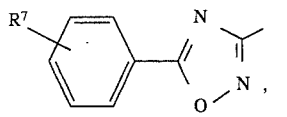

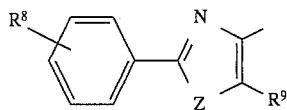

or

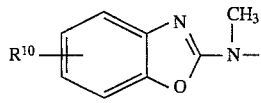

wherein R⁷, R⁸ and R¹⁰ are independently halogen, trifluoromethyl, alkyl, alkoxy, methanesulfonyl or trifluoromethanesulfonyl; R⁹ is hydrogen or methyl; and Z is O or S, or a pharmaceutically acceptable salt thereof.

The PCT patent application WO 92/03425 discloses intermediates to antidiabetic compounds which correspond to the Formula I compounds wherein R¹ is

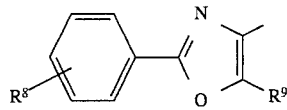

R³ is H and R⁴ is

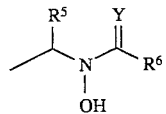

and further where R⁵ is hydrogen and R⁶ is —NH₂.

The compounds of Formula I which are novel are represented by Formula Ia:

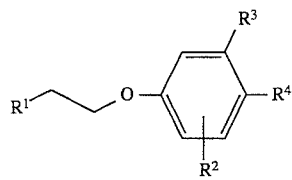

Ia wherein: R² is hydrogen, halogen or alkyl;

one of R³ and R⁴ is hydrogen and the other is

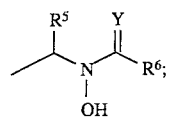

Y is O or S;

R⁵ is hydrogen or methyl

R⁶ is —NH₂, —CH₃ or —OCH₃;

and R¹ is

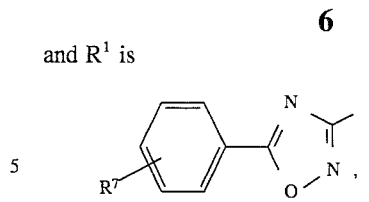

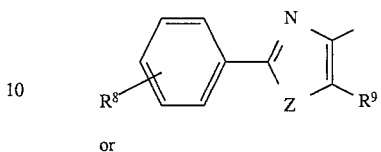

or

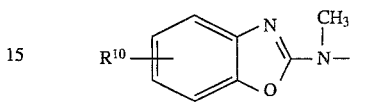

wherein R⁷, R⁸ and R¹⁰ are independently hydrogen, halogen, trifluoromethyl, $C_1$–$C_6$ alkyl, $C_1$–$C_6$ alkoxy, methanesulfonyl or trifluoromethanesulfonyl; R⁹ is hydrogen or methyl; and Z is O or S, or a pharmaceutically acceptable salt thereof with a proviso that when R³ is H and R⁶ is —NH₂, R¹ cannot be

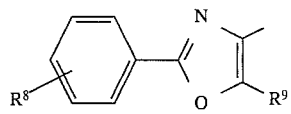

Under Formulas I and Ia, halogen means fluorine, chlorine, bromine or iodine. The term pharmaceutically acceptable salt includes hydrates, solvates and acid addition salts which can be formed from an invention compound and a pharmaceutically acceptable mineral or organic acid salt including but not limited to the hydrochloride, hydrobromide, sulfate, phosphate, fumarate, acetate, maleate, succinate, tartrate, cyclohexylsulfamate, citrate and methanesulfonate salts.

It is one object of this invention to provide a method of inhibiting 5-lipoxygenase and inhibiting metabolic oxidation of lipids, especially LDL. Other objects of this invention are to provide methods of treatment for diseases of inflammation, allergic responses, and treatment of atherosclerosis. Still other objects are to provide pharmaceutical compositions and novel compounds.

DETAILED DESCRIPTION OF THE INVENTION

The starting heterocyclic intermediates of the formula

are prepared according to standard literature procedures. For example, 4-(1'-hydroxyethyl)-5-methyl-2-phenyloxazoles can be prepared according to scheme (a) (European Patent EP 0177353A2).

Scheme (a)

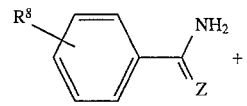
+

-continued
Scheme (a)

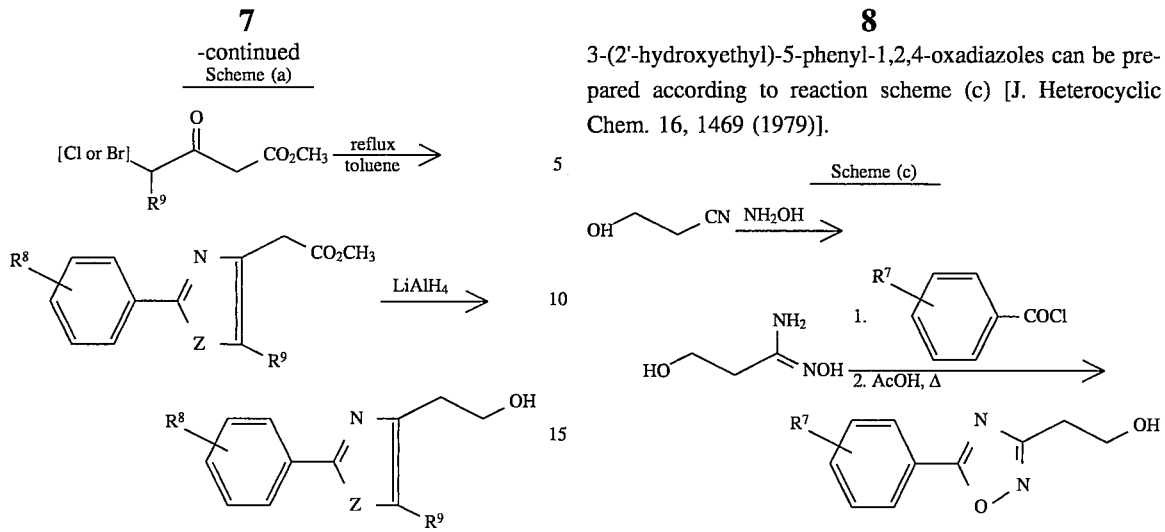

2-[N-Methyl-N-(2-benzoxazolyl)amino]ethanols can be prepared by reaction scheme (b) (U.S. Pat. No. 5,002,953).

Scheme (b)

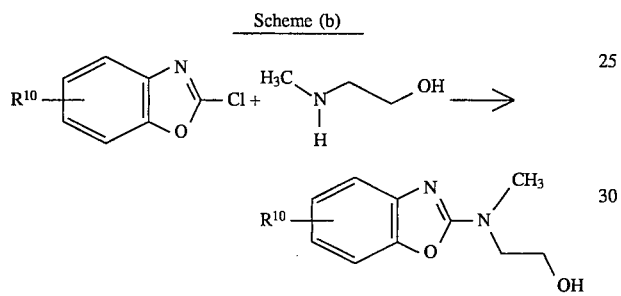

3-(2'-hydroxyethyl)-5-phenyl-1,2,4-oxadiazoles can be prepared according to reaction scheme (c) [J. Heterocyclic Chem. 16, 1469 (1979)].

Scheme (c)

The invention compounds of Formulas I and Ia can be prepared according to the following reaction schemes (d)–(h). Schemes (d)–(f) illustrate the procedures used to prepare compounds where $R^5$ is —$NH_2$.

Scheme (d): $R^1$ is 5-phenyl-1,2,4-oxadiazol-3-yl.

Scheme (d):
$R^1$ is 5-phenyl-1,2,4-oxadiazol-3-yl.

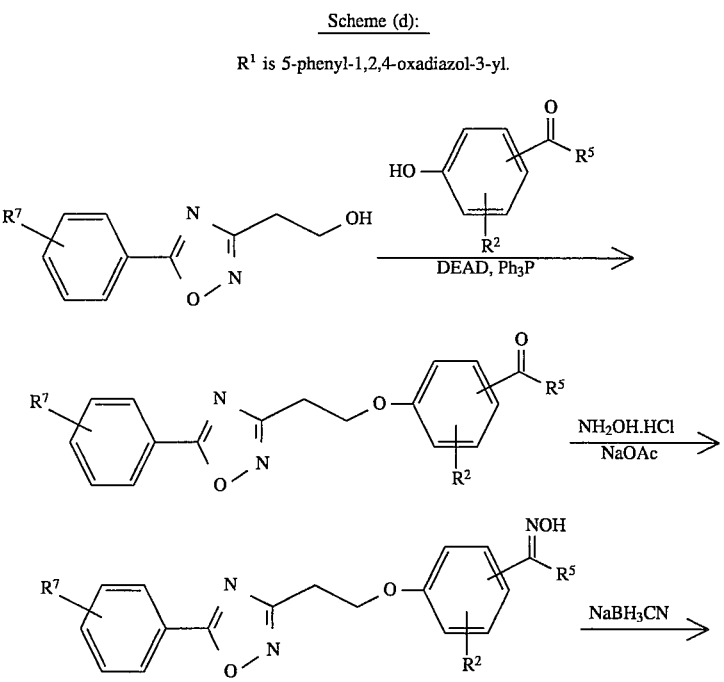

-continued
Scheme (d):
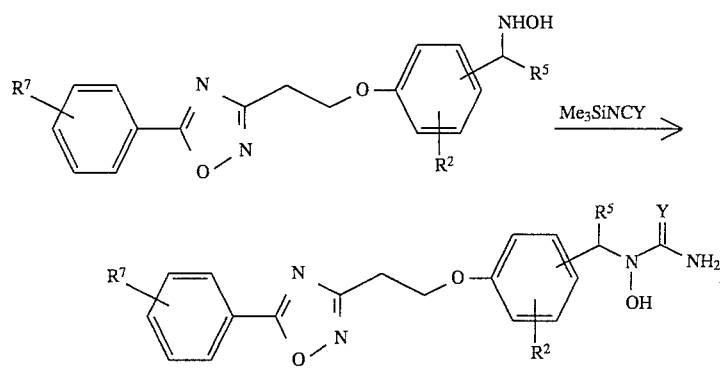
Scheme (e):
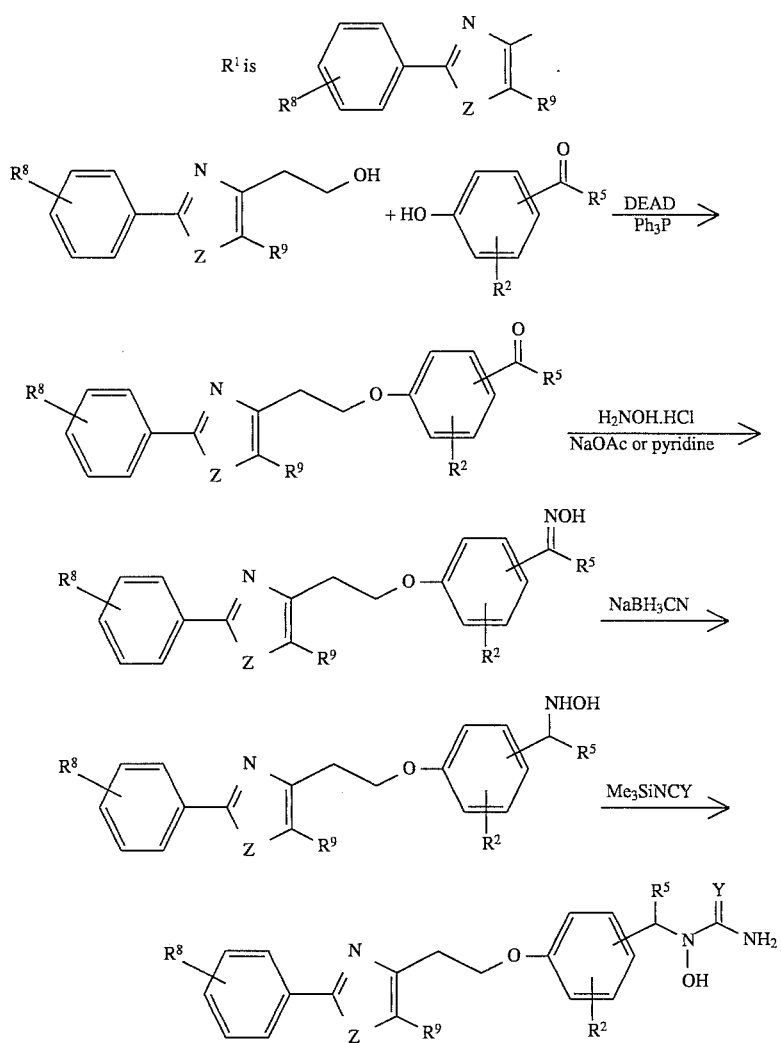

Scheme (f):

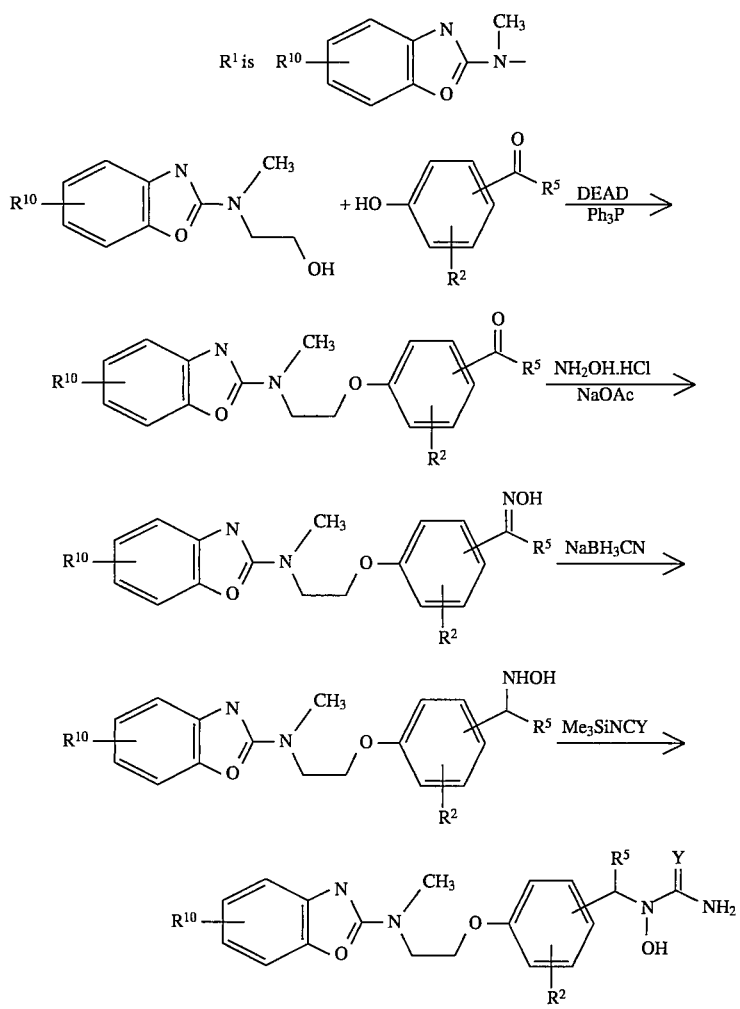

Where $R^6$ is —$CH_3$, the Formula I compounds are prepared from the intermediate hydroxyamino compounds of schemes (d)–(f) above utilizing acetic anhydride as follows (Scheme (g))

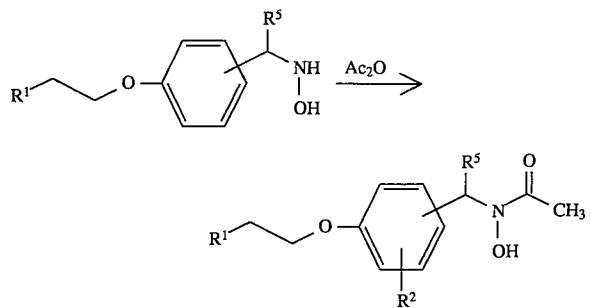

Where $R^6$ is —$OCH_3$, the Formula I compounds are prepared from the intermediate hydroxyamino compounds of schemes (d)–(f) above utilizing methyl chloroformate as shown below (Scheme (h)).

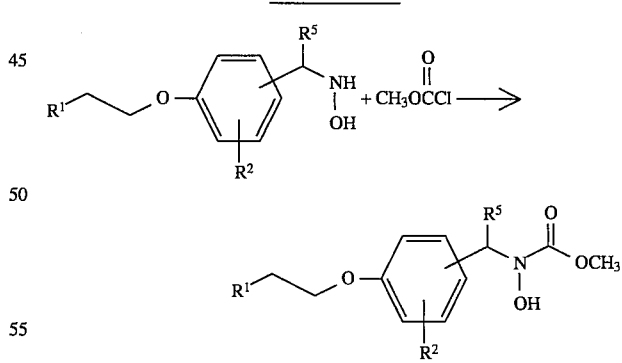

In the above synthetic reaction schemes the variables $R^1$–$R^{10}$, Y and Z are as defined under Formula I.

The following specific examples are included to illustrate the above synthetic procedures. These examples are not to be construed as limiting the scope of this invention. The reagents and intermediates used in the examples are either commercially available or can be prepared according to standard literature procedures by one skilled in the art of organic synthesis.

EXAMPLE 1

1-Hydroxy-1-[4-[2-(5-methyl-2-phenyl-oxazol-4-yl)-ethoxy-benzyl]-urea

Step a) 4-[2-(5-methyl-2-phenyl-oxazol-4-yl)-ethoxyl]-benzaldehyde

In to a cold (0° C.) solution of 4-(2'-hydroxy-ethyl)-5-methyl-2-phenyloxazole (5.0 g, 24.63 mmol), triphenylphosphine (6.45 g, 24.63 mmol), and 4-hydroxybenzaldehyde (3.0 g, 24.63 mmol) in THF (100 mL) was added dropwise diethylazodicarboxylate (3.87 mL, 24.63 mmol). The mixture was allowed to come to room temperature and stirred for 48 hours, poured into $H_2O$ and extracted with EtOAc. The organic extracts were dried over $MgSO_4$. Evaporation and purification by flash chromatography on silica gel (hexane/EtOAc 4/1 ) gave a yellow solid (5.9 g, 78% yield, m.p. 77°–78° C.).

Analysis for: $C_{19}H_{12}NO_3$ Calc'd: C, 74.25; H, 5.58; N, 4.56 Found: C, 74.11; H, 5.54; N, 4.55

Step b) 4-[2-(5-Methyl-2-phenyl-oxazol-4-yl)-ethoxy]-benzaldehyde oxime

To a solution of 4-[2-(5-methyl-2-phenyl-oxazol-4-yl)-ethoxy]-benzaldehyde (5.4 g, 17.59 mmol) in EtOH (300 mL) was added a mixture of hydroxylamine hydrochloride (3.67 g, 52.76 mmol) and sodium acetate (5.77 g, 70.36 mmol) in $H_2O$ (50 mL). The mixture was stirred at room temperature for 24 hours, poured into $H_2O$ and extracted with EtOAc. The organic extracts were dried over $MgSO_4$. Evaporation and crystallization from acetone/ether (after cooling to 0° C.) gave a white solid (5.1 g, 90% yield, m.p. 153°–155° C.).

Analysis for: $C_{19}H_{18}N_2O_3$ Calc'd: C, 70.79; H, 5.63; N, 8.69 Found: C, 70.85; H, 5.64; N, 8.84

Step c) N-[4-[2-(5-Methyl-2-phenyl-oxazol-4-yl)ethoxy]-benzyl-hydroxylamine

To a solution of 4-[2-((5-methyl-2-phenyl-oxazol-4-yl)-ethoxy]-benzaldehyde oxime (4.0 g, 19.42 mmol) in MeOH (300 mL), and THF (50 mL) were added sodium cyanoborohydride (3.87 g, 62.11 mmol) and methyl orange (indicator, 10 mg). A solution of 4N HCl in dioxane was added dropwise in order to maintain the solution pH~3–4. After a steady red color was obtained, the mixture was poured into $H_2O$, basified with 1N NaOH and extracted with EtOAc. The organic extracts were dried over $MgSO_4$. Evaporation and purification by flash chromatography, on silica gel (EtOAc/MeOH 10/1 ) gave a white solid (3.4 g, 85% yield, m.p. 95°–96° C.).

Analysis for: $C_{19}H_{20}N_2O_3$ Calc'd: C, 70.35; H, 6.21; N, 8.64 Found: C, 70.43; H, 6.24; N, 8.91

Step d) 1-Hydroxy-1-[4-[2-(5-methyl-2-phenyl-oxazol-4-yl)-ethoxy-benzyl]-urea

To a solution of N-[4-[2-(5-methyl-2-phenyl-oxazol-4-yl)-ethoxy]-benzyl]-hydroxylamine (2.5 g, 7.71 mmol) in dioxane (30 mL) was added trimethylsilylisocyanate (1.4 mL, 10.0 mmol). After stirring for 2 hours at room temperature the mixture was poured into $H_2O$, acidified with HCl (2N), and extracted with EtOAc. The organic extracts were dried over $MgSO_4$. Evaporation and crystallization from acetone/ether (after cooling to 0° C.), gave a white solid (1.96 g, 69% yield, m.p. 128°–129° C.).

Analysis for: $C_{20}H_{21}N_3O_4$ Calc'd: C, 65.38; H, 5.76; N, 11.44 Found: C, 65.54; H, 5.82; N, 11.24

EXAMPLE 2

1-Hydroxy-1-[3-[2-(5-methyl-2-phenyl-oxazol-4-yl)-ethoxy]-benzyl]-urea

The title compound was prepared in substantially the same manner as described in Example 1, steps a–d. 3-Hydroxybenzaldehyde was used in place of 4-hydroxybenzaldehyde. The title compound was obtained as a white solid, m.p. 152°–153° C.

Analysis for: $C_{20}H_{21}N_3O_4$ Calc'd: C, 65.38; H, 5.76; N, 11.49 Found: C, 65.63; H, 5.91; N, 11.34

EXAMPLE 3

1-Hydroxy-1-[4-[2-[2-(4-methoxy-phenyl)-5-methyl-oxazol-4-yl]-ethoxy]-benzyl]-urea The title compound was prepared in substantially the same manner as described in Example 1, steps a–d, and was obtained as a white solid, m.p. 100°–101 ° C.

Analysis for: $C_{21}H_{23}N_3O_5$ Calc'd: C, 63.47; H, 5.83; N, 10.57 Found: C, 63.63; H, 5.86; N, 10.45

EXAMPLE 4

1-Hydroxy-1-[1-[4-[2-(4-methyl-2-phenyl-oxazol-4-yl)-ethoxy]-phenyl]-ethyl]-urea The title compound was prepared in substantially the same manner as described in Example 1, steps a–d. 4'-Hydroxyacetophenone was used in place of 4-hydroxybenzaldehyde. The title compound was obtained as a white solid, m.p. 136°–138° C.

Analysis for: $C_{21}H_{23}N_3O_4$ Calc'd: C, 66.13; H, 6.08; N, 11.02 Found: C, 65.78; H, 6.35; N, 11.19

EXAMPLE 5

1-Hydroxy-1-[1-[3-[2-(5-methyl-2-phenyl-oxazol-4-yl)-ethoxy]-phenyl]-ethyl]-urea The title compound was prepared in substantially the same manner as described in Example 1, steps a–d. 3'-Hydroxyacetophenone was used in place of 4-hydroxybenzaldehyde. The title compound was obtained as a white solid, m.p. 153°–154° C.

Analysis for: $C_{21}H_{23}N_3O_4$ Calc'd: C, 66.13; H, 6.08; N, 11.02 Found: C, 66.26; H, 6.06; N, 10.75

EXAMPLE 6

1-[4-[2-[2-(2-Fluoro-phenyl)-5-methyl-oxazol-4-yl]-ethoxy]-benzyl]-1-hydroxy-urea The title compound was prepared in substantially the same manner as described in Example 1, steps a–d, and was obtained as a white solid, m.p. 151°–152° C.

Analysis for: $C_{20}H_{20}FN_3O_4$ Calc'd: C, 62.33; H, 5.23; N, 10.90 Found: C, 62.29; H, 5.17; N, 10.54

EXAMPLE 7

1-[4-[2-[2-(3-Fluoro-phenyl)-5-methyl-oxazol-4-yl)-ethoxy-benzyl]-1-hydroxy-urea The title compound was prepared in substantially the same manner as described in Example 1, steps a–d, and was obtained as a white solid, m.p. 142°–143° C.

Analysis for: $C_{20}H_{20}FN_3O_4$ Calc'd: C, 62.33; H, 5.23; N, 10.90 Found: C, 62.43; H, 5.18; N, 10.55

EXAMPLE 8

1-[4-[2-[2-(4-Fluoro-phenyl)-5-methyl-oxazol-4-yl)-ethoxy]-benzyl]-1-hydroxy-urea The title compound was prepared in substantially the same manner as described in Example 1, steps a–d, and was obtained as a white solid, m.p. 158°–160° C.

Analysis for: $C_{20}H_{20}FN_3O_4$ Calc'd: C, 62.33; H, 5.23; N, 10.90 Found: C, 62.43; H, 5.18; N, 10.51

EXAMPLE 9

1-[2,6-Dimethyl-4-[2-(5-methyl-2-phenyl-oxazol-4-yl)-ethoxy]-benzyl]-1-hydroxy-urea The title compound was prepared in substantially the same manner as described in Example 1, steps a–d, and was obtained as a white solid, m.p. 170°–171° C.

Analysis for: $C_{22}H_{25}N_3O_4$ Calc'd: C, 66.82; H, 6.37; N, 10.63 Found: C, 66.39; H, 6.33; N, 10.30

EXAMPLE 10

1-[4-[2-[2-(3,5-(Di-tert-butyl)-4-hydroxy-phenyl)-5-methyl-oxazol-4-yl]-ethoxy]-benzyl-1-hydroxy-urea The title compound was prepared in substantially the same manner as described in Example 1, steps a–d, and was obtained as a white solid, m.p. 93°–95° C.

Analysis for: $C_{28}H_{37}N_3O_5$ Calc'd: C, 67.86; H, 7.53; N, 8.28 Found: C, 68.05; H, 7.63; N, 7.95

EXAMPLE 11

1-Hydroxy-1-[4-[2-(5-methyl-2-(p,tolyl)-oxazol-4-yl]-ethoxyl-benzyl]-urea

The title compound was prepared in substantially the same manner as described in Example 1, steps a–d, and was obtained as a white solid, m.p. 145°–146° C.

Analysis for: $C_{21}H_{23}N_3O_4$ Calc'd: C, 66.13; H, 6.08; N, 11.07 Found: C, 66.16; H, 6.13; N, 11.33

EXAMPLE 12

1-[3-Fluoro-4-[2-(5-methyl-2-phenyl-oxazol-4-yl)-ethoxy]-benzyl]-1-hydroxy-urea

The title compound was prepared in substantially the same manner as described in Example 1, steps a–d, and was obtained as a white solid, m.p. 135°–136° C.

Analysis for: $C_{20}H_{20}FN_3O_4$ Calc'd: C, 62.23; H, 5.23; N, 10.90 Found: C, 62.32; H, 5.24; N, 10.51

EXAMPLE 13

1-Hydroxy-1-[4-[2-[5-methyl-2-(4-trifluoromethyl-phenyl)-oxazol-4-yl]ethoxy]-benzyl]-urea The title compound was prepared in substantially the same manner as described in Example 1, steps a–d, and was obtained as a white solid, m.p. 156°–157° C.

Analysis for: $C_{21}H_{20}F_3N_3O_4$ Calc'd: C, 57.93; H, 4.63; N, 9.65 Found: C, 57.70; H, 4.09; N, 9.64

Example 14

1-[3-Fluoro-4-[2-[5-methyl-2-(4-trifluoromethyl-phenyl)-oxazol-4-yl]-ethoxy]-benzyl]-1-hydroxy- urea The title compound was prepared in substantially the same manner as described in Example 1, steps a–d, and was obtained as a white solid, m.p. 144°–146° C.

Analysis for: $C_{21}H_{19}F_4N_3O_4$ Calc'd: C, 55.63; H, 4.22; N, 9.27 Found: C, 55.40; H, 4.38; N, 9.06

EXAMPLE 15

1-[3,5-Dichloro-4-[2-[5-methyl-2-(4-trifluoromethyl-phenyl)-oxazol-4-yl]ethoxy]-benzyl]-1-hydroxy-urea The title compound was prepared in substantially the same manner as described in Example 1, steps a–d, and was obtained as a white solid, m.p. 137°–139° C.

Analysis for: $C_{21}H_{18}Cl_2F_3N_3O_4$ Calc'd: C., 50.02; H, 3.60; N, 8.33 Found: C, 50.24; H, 3.46; N, 7.99

EXAMPLE 16

1-Hydroxy-1-[4-[2-[5-methyl-2-(4-trifluoromethylsulfanyl-phenyl)-oxazol-4-yl]-ethoxy]-benzyl]-urea The title compound was prepared in substantially the same manner as described in Example 1, steps a–d, and was obtained as a white solid, m.p. 157°–159° C.

Analysis for: $C_{21}H_{20}F_3N_3O_4S$ Calc'd: C, 53.96; H, 4.31; N, 8.99 Found: C, 53.98; H, 4.18; N 8.72

EXAMPLE 17

1-Hydroxy-1-[4-[2-[2-phenyl-thiazol-4-yl)-ethoxyl-benzyl]-urea

The title compound was prepared in substantially the same manner as described in Example 1 steps a–d, and was obtained as a white solid, m.p. 137°–138° C.

Analysis for: $C_{19}H_{19}N_3O_3S$ Calc'd: C, 61.77; H, 5.18; N, 11.37 Found: C, 61.86; H, 5.22; N, 11.29

EXAMPLE 18

1-Hydroxy-1-[4-[2-(2-phenyl-thiazol-4-yl)-ethoxy-benzyl]-thiourea step a) 4-(2-phenyl-thiazol-4-ylethoxy)benzaldehyde In to a cold (0° C.) solution of 4-(2'-hydroxy-ethyl)-2-phenylthiazole (3.5 g, 17.05 mmol), triphenylphosphine (5.0 g, 19.0 mmol), 4-hydroxybenzaldehyde (2.1 g, 17.05 mmol) in THF (100 mL) was added dropwise diethylazodicarboxylate (3.3 g, 19.0 mmol). The mixture was allowed to come to room temperature and stirred for 48 hours, poured into $H_2O$ and extracted with EtOAc. The organic extracts were dried over $MgSO_4$. Evaporation and purification by flash chromatography on silica gel (hexane/EtOAc 3/1 ) gave a white solid (3.5 g, 66% yield, m.p. 68°–70° C.).

Analysis for: $C_{18}H_{15}NO_2S$ Calc'd: C, 69.88; H, 4.89; N, 4.53 Found. C, 69.86; H, 4.95; N, 4.58 step b) 4-(2-phenyl-thiazol-4-ylethoxy)benzaldehyde oxime

In to a solution of 4-(2-phenyl-thiazol-4-ylethoxy)benzaldehyde (3.4 g, 11.0 mmol) in EtOH (80 mL) were added hydroxylamine hydrochloride (1.6 g, 22.0 mmol) and pyridine (35 mL). The mixture was stirred at 60 ° C. for 1.5 hours, poured into H$_2$O and extracted with EtOAc. The organic extracts were dried over MgSO$_4$. Evaporation and crystallization from EtOAc gave a white solid (2.2 g, 81% yield, m.p. 142°–144° C.).

Analysis for: C$_{18}$H$_{16}$N$_2$O$_2$S Calc'd: C, 66.65; H, 4.97; N, 8.64 Found: C, 66.54; H, 4.99; N, 8.61 step c) N-4-(2-phenyl-thiazol-4-ylethoxy)benzyl-hydroxylamine

In to a solution of 4-(2-phenyl-thiazol-4-ylethoxy)benzaldehyde oxime (2.8 g, 8.6 mmol) in AcOH (100 mL) was added sodium cyanoborohydride (3.87 g, 62.11 mmol) over a 15 minutes period. After stirring at room temperature for 2 hours, the mixture was concentrated to one third of its volume, and poured into NaOH (2 N, 800 mL). The precipitated solids were filtered off and then dissolved in hot EtOAc (500 mL). The organic extracts were washed with water, brine and dried over MgSO$_4$. Evaporation and crystallization from EtOAc/hexane, gave a white solid (2.2 g, 78.4% yield, m.p. 110°–112° C.).

Analysis for: C$_{18}$H$_{18}$N$_2$O$_2$S Calc'd: C, 66.23; H, 5.56; N, 8.58 Found: C, 65.98; H, 5.59; N, 8.56 step d) 1-Hydroxy-1-[4-[2-(2-phenyl-thiazol-4-yl)-ethoxybenzyl]-thiourea

In to a solution of N-4-(2-phenyl-thiazol-4-ylethoxy)benzyl-hydroxylamine (0.9 g, 2.76 mmol) in dioxane (50 mL) was added trimethylsilylisothiocyanate (1.4 g, 11.0 mmol). After stirring for 3 hours at room temperature the mixture was poured into aqueous NH$_4$Cl, and extracted with EtOAc. The organic extracts were dried over MgSO$_4$. Evaporation and crystallization from EtOAc, gave a white solid (0.48 g, 46% yield, m.p. 151°–155° C.).

Analysis for: C$_{19}$H$_{19}$N$_3$O$_2$S$_2$ Calc'd: C, 59.20; H, 4.79; N, 10.90 Found: C, 59.30; H, 4.98; N, 10.67

EXAMPLE 19

1-Hydroxy-1-[4-[2-[2-(4-trifluoromethyl-phenyl)-thiazol-4-yl]-ethoxy]benzyl]-urea The title compound was prepared in substantially the same manner as described in Example 1, steps a–d, and was obtained as a white solid, m.p. 146°–147° C.

Analysis for: C$_{20}$H$_{18}$F$_3$N$_3$O$_3$S Calc'd: C, 54.92; H, 4.15; N, 8.61 Found: C, 55.26; H, 4.19; N, 9.25

Example 20

1-Hydroxy-1-[3-[2-[2-(4-trifluoromethyl-phenyl)-thiazol-4-yl]-ethoxy]benzyl]-urea The title compound was prepared in substantially the same manner as described in Example 1, steps a–d, and was obtained as a white solid, m.p. 118°–120° C.

Analysis for: C$_{20}$H$_{18}$F$_3$N$_3$O$_3$S Calc'd: C, 54.92; H, 4.15; N, 9.61 Found: C, 54.96; H, 4.07; N, 9.38

EXAMPLE 21

1-hydroxy-1-[4-[2-(5-phenyl-[1,2,4]-oxadiazol-3-yl)-ethoxy]-benzyl]-urea

Step a). 4-[2-(5-phenyl-[1,2,4]-oxadiazol -3-yl)-ethoxy]-benzaldehyde

To a cold (0° C.) solution of 3-[2'-hydroxyethyl]-5-phenyl-(1, 2, 4)-oxadiazole (6.0 g, 3158 mmol), triphenylphosphine (9.1 g, 34.74 mmol), 4-hydroxybenzaldehyde (3.9g, 31.58 mmol) in THF (100 mL) was added dropwise diethylazodicarboxylate (6.05 g, 34.74 mmol). The mixture was allowed to come to room temperature and stirred for 24 hours, poured into H$_2$O and extracted with EtOAc. The organic extracts were dried over MgSO$_4$. Evaporation and purification by flash chromatography, on silica gel (hexane/EtOAc 3/1 ) gave a white solid (4.5 g, 49% yield, m.p 130°–131° C.).

Step b) 4-[2-(5-phenyl-[1,2,4]-oxadiazol, 3-yl)-ethoxy]-benzaldehyde oxime

To a solution of [4-[2-(5-phenyl-[1,2,4]-oxadiazol-3-yl)-ethoxy]-benzaldehyde (4.5 g, 15.3 mmol) in EtOH (150 mL) was added a mixture of hydroxylamine hydrochloride (1.5 g, 21.4 mmol) and sodium acetate (1.0 g, 23.0 mmol) in H$_2$O (20 mL). The mixture was stirred at room temperature for 24 hours, poured into H$_2$O and extracted with EtOAc. The organic extracts were dried over MgSO$_4$. Evaporation and crystallization from acetone/ether gave a white solid (3.8 g, 90% yield, m.p 180°–181° C.).

Step c) N-[[4-[2-(5-phenyl-[1,2,4]-oxadiazol-3-yl)-ethoxy]-benzyl-hydroxylamine

To a solution of 4-[2-(5-phenyl-[1,2,4]-oxadiazol-3-yl)-ethoxy]-benzaldehyde oxime (3.8 g, 12.30 mmol) in MeOH (100 mL) and THF (125 mL) were added sodium cyanoborohydride (4.7 g, 73.8 mmol) and methyl orange (indicator, 10 mg). A solution of 4N HCl in dioxane was added dropwise in order to maintain the solution pH~3–4. After a steady red color was obtained, the mixture was poured into H$_2$O, basified with 1N NaOH and extracted with EtOAc. The organic extracts were dried over MgSO$_4$. Evaporation and purification by flash chromatography, on silica gel (EtOAc/MeOH 10/1 ) gave a white solid (3.55 g, 93% yield, 175°–178° C.).

Step d) 1-hydroxy-1-[4-[2-(5-phenyl -[1,2,4]-oxadiazol-3-yl)-ethoxy]-benzyl]-urea To a solution of N-[4-[2-(5-phenyl-[1,2,4]-oxadiazol-3-yl)-ethoxy]-benzyl]-hydroxylamine (1.5 g, 4.82 mmol in dioxane (70 mL) was added trimethylsilylisocyanate (o.84 g, 7.23 mmol). After stirring for 2 hours at room temperature the mixture was poured into H$_2$O, acidified with HCl (2N), and extracted with EtOAc. The organic extracts were dried over MgSO$_4$. Evaporation and crystallization from acetone/ether (after cooling to 0° C.), gave a white solid (1.2 g, 70% yield, m.p. 135°–136° C.).

Analysis for: C$_{18}$H$_{18}$N$_4$O$_4$ Calc'd: C, 61.00; H, 5.12; N, 15.81 Found: C, 61.25; H, 5.18; N, 15.91

EXAMPLE 22

1-[4-[2-(-Benzoxazol-2-yl-methyl-amino)-ethoxyl,benzyl]-1-hydroxy-urea

The title compound was prepared in substantially the same manner as described in Example 1, steps a–d. 2-[N-methyl-N-(2-benzoxazolyl)-amino] ethanol was used in place of 4-(2'-hydroxy-ethyl)- 5-methyl-2-phenyloxazole. The title compound was obtained as a white solid, m.p. 175°–176° C.

Analysis for: C$_{18}$H$_{20}$N$_4$O$_4$ Calc'd: C, 60.66; H, 5.66; N, 15.72 Found: C, 60.48; H, 5.75; N, 15.40

EXAMPLE 23

N-[4-[2-(Benzoxazol -2-yl-methyl-amino)-ethoxy]-benzyl]-N-hydroxyacetamide

To a mixture of N-[4-[2-(benzoxazol-2-yl-methyl-amino)-ethoxy]-benzyl]-hydroxylamine (1.5 g, 4.78 mmol)

in THF (5 mL) was added acetic anhydride (0.49 g, 4.78 mmol). The mixture was stirred for 1 hour and the volatiles were removed in vacuo. Crystallization from EtOAc/hexane, gave a white solid (1.3 g, 77% yield, m.p. 135°–136° C.).

Analysis for: $C_{19}H_{21}N_3O_4$ Calc'd: C, 64.21; H, 5.96; N, 11.82 Found: C, 64.59; H, 6.11; N, 11.65

EXAMPLE 24

[[4-[2-Benzoxazol-2-yl-methyl-amino)-ethoxy]-benzyl]-methyl]-carbamic acid methyl ester To a cold (0° C.) solution of N-[4-[2-benzoxazol-2-yl-methyl-amino)-ethoxy]-benzyl]-hydroxylamine (1.3 g, 4.15 mmol) in THF (10 mL) were added methyl chloroformate (0.44 g, 4.7 mmol), and triethylamine (0.63 g, 6.2 mmol). The mixture was allowed to come to room temperature, stirred for 20 minutes, poured into $H_2O$ and extracted with EtOAc. The organic extracts were dried over $MgSO_4$. Evaporation and crystallization from EtOAc/hexane, gave a white solid (1.1 g, 71% yield, m.p. 125°–126° C.).

Analysis for: $C_{19}H_{21}N_3O_5$ Calc'd: C, 61.45; H, 5.70; N, 11.31 Found: C, 61.12; H, 5.71; N, 10.97

PHARMACOLOGY

Lipoxygenase inhibiting activity and inhibition of $Cu^{+2}$ mediated peroxidation of LDL by the Formula I compounds is demonstrated in several standard pharmacological assays.

1. Inhibition of 5-Lipoxygenase in Human Whole Blood

Blood is obtained in 50–100 ml quantities from male donors. White blood cell counts and differentials are made. Two ml of blood are placed in a 15 ml polypropylene test tube. Test compounds are solubilized in dimethylsulfoxide and diluted in 1:10 in 10% bovine serum albumin in phosphate buffered saline, pH 7.4 resulting in a final dimethylsulfoxide concentration of 0.1% in the blood. Then, solutions of test compounds are added to the blood in a shaking water bath at 37° C. for 10 minutes prior to the addition of 30 µM calcium ionophore (A23187, Sigma). After ionophore administration, whole blood samples are mixed and incubated for 20 minutes at 37° C. in a shaking water bath. Incubation is terminated by placing samples in an ice bath and immediately adding ethylene glycol-bis-(β-aminoethyl ether)-N,N,N',N'-tetraacetic acid (10 mM). Samples are mixed and centrifuged at 1200×g for 15 minutes at 4° C. Preparation of samples for evaluation by RIA or ELISA is carried out by the following protocol. Plasma is removed from sample tubes, placed in 15 ml polypropylene test tubes containing 8 ml methanol, and then vortexed to precipitate protein. Samples are stored at −70° C. overnight. The next day, samples are centrifuged at 200×g for 15 minutes at 4° C. to pellet the precipitate. Samples are dried in a Savant SpeedVac Concentrator, Model SVC 200H, reconstituted to original volume with ice cold RIA or ELISA buffer, and stored at −70° C. until assayed. The assay for eicosanoids ($LTB_4$, $TxB_2$, and $PGE_2$) is performed as described by the manufacturer of the [$_3$H]-RIA kit or ELISA kit ($LTB_4$Amersham, $TxB_2$ and $PGE_2$-Caymen Chemical).

The total eicosanoid level in 2 ml of blood is calculated and reported as ng/$10^6$ neutrophils. Significance is determined by a one-way analysis of variance with least significant difference (LSD) comparisons to control (p≦0.05) and $IC_{50}$'s (µM) are determined by regression analysis (Finney, 1978). Drug effects are expressed as percent change from control values. The results for compounds of this invention tested in this assay are presented in Table I.

TABLE I

| Compound of Example No. | Dose (µM) | % Inhibition of $LTB_4$ |
| --- | --- | --- |
| 1 | 1 | 55 |
| 2 | 1 | 51 |
| 3 | 1 | 57 |
| 4 | 10 | 60 |
| 5 | 1 | 34 |
| 6 | 1 | 54 |
| 7 | 1 | 63 |
| 8 | 1 | 70 |
| 9 | 10 | 42 |
| 10 | 10 | 83 |
| 11 | 1 | 40 |
| 12 | 1 | 71 |
| 13 | 1 | 47 |
| 14 | 1 | 36 |
| 15 | 1 | 38 |
| 16 | 1 | 50 |
| 17 | 10 | 93 |
| 18 | 10 | 94 |
| 19 | 1 | 57 |
| 20 | 1 | 30 |
| 21 | 1 | 70 |
| 22 | 10 | 60 |
| 23 | 1 | 39 |
| 24 | 10 | 77 |

2. Ex-Vivo Measurement of Lipoxygenase Inhibition in Orally Dosed Rats

Male Sprague Dawley rats (Charles River) weighing between 180 g and 200 g were dosed orally with an invention compound (1–25 mg/kg, po) suspended in 0.5% Tween 80®. After an interval of 3 or 6 hours, the rats were anesthetized with metofane (n=4/group) and blood collected in heparinized tubes. White blood cell counts and differentials were made. One ml of blood from each animal was placed in a 5 ml plastic tube in a shaker bath at 37° C. A23187 at a final concentration of 10 µM was added to the blood and the blood vortexed and incubated for 15 min at 37° C. with gentle shaking. Incubation was terminated by vortexing sample and centrifuging immediately at 1200 ×G for 15 min at 4° C. The plasma was transferred to 15 ml plastic tubes each containing 8 ml of methanol to precipitate protein followed by vortexing. The samples were stored at −70° C. overnight and the next day the samples were centrifuged at 800 ×G for 15 min to pellet the precipitate. The samples were dried in a Savant SpeedVac Concentrator Model SVC 200H and reconstituted to the original volume with cold RIA or ELISA buffer. The reconstituted samples were stored at −70° C. until assayed. The assay for $LTB_4$ was performed according to the directions of the [$^3$H]RIA kit or ELISA kit (Seragen). The total metabolite level in 1 ml of blood is calculated and reported as ng/$10^6$ neutrophils. Significance is determined by a one-way analysis of variance with LSD comparisons to control (p≦0.05). Drug effects are expressed as percent change from control values and data for invention compounds is presented in Table II.

TABLE II

| Compound of Example No. | Dose (µM) | Pretreatment period (hr) | % Inhibition of $LTB_4$ |
| --- | --- | --- | --- |
| 1 | 25 | 3 | 79 |
| 2 | 25 | 3 | 21 |
| 3 | 25 | 3 | 32 |
| 4 | 25 | 3 | 57 |
| 6 | 10 | 3 | 71 |
| 7 | 10 | 3 | 79 |

TABLE II-continued

| Compound of Example No. | Dose (μM) | Pretreatment period (hr) | % Inhibition of LTB$_4$ |
|---|---|---|---|
| 8 | 10 | 3 | 66 |
| 10 | 10 | 3 | 44 |
| 12 | 10 | 3 | 52 |
| 13 | 1 | 6 | 50 |
| 21 | 5 | 6 | 60 |
| 23 | 25 | 3 | 78 |

3. Reverse Passive Arthus Reaction

A reverse passive Arthus reaction is induced in the pleural cavity of male Lewis rats (150–200 g; fasted overnight prior to use) by the intravenous administration of bovine serum albumin (BSA; 4 mg/0.2 ml) followed 30 minutes later by the injection of rabbit anti-BSA (1 mg/0.2 ml; lyophilized IgG fraction; Organon Teknika, West Chester, Pa.) into the right pleural space under halothane anesthesia. Drugs or vehicle (0.5% Tween-80) control are administered orally in a volume of 1 ml/100 g body weight at 1 hour prior to the anti-BSA. Animals are sacrificed at either the time of peak eicosanoid production (i.e. 5 minutes after anti-BSA for immunoreactive TxB$_2$, 10 minutes for immunoreactive LTB$_4$, 20 minutes for immunoreactive LTC$_4$) or at the time of peak neutrophil infiltration (4 hours after anti-BSA) by $CO_2$ inhalation. The pleural cavity is then exposed, the fluid exudate removed by gentle vacuum aspiration and the volume of exudate is recorded. For the determination of cellular infiltration, the pleural cavity is rinsed with 3 ml of 0.1% EDTA in sterile saline, and the recovered wash is pooled with the exudate. Cell number is determined on a model ZBI Coulter counter. For determination of eicosanoid production, undiluted pleural exudate is microfuged and the supernatant is extracted with ethanol (8–10 times volume). Extracts are either stored at −20° C., or are evaporated to dryness under a stream of $N_2$ and reconstituted in radioimmunoassay (RIA) buffer.

Eicosanoids are quantitated by RIA according to the procedure specified by the RIA kit manufacturer (Advanced Magnetics, Cambridge, Mass.). Briefly, 100 μl of $^3$H-labeled eicosanoid and 100 μl of specific antibody are sequentially added to 100 μl of extracted pleural exudate in BGG-phosphate buffer which contains 0.01 M phosphate, 0.1% bovine gamma globulin and 0.1% sodium azide at pH 7.0. Antibody-bound eicosanoid is separated from unbound eicosanoid by the addition of 750 μl of dextran (0.4%)-coated charcoal (Norit A) containing 0.1% sodium azide. The mixture is centrifuged at 2000 RPM at 5° C. for 15 minutes to pellet the charcoal and adsorbed unbound eicosanoid. Antibody-bound labeled eicosanoid is quantitated by counting in a liquid scintillation counter, and is correlated to concentration by a standard curve.

The activity of standard drugs in this assay is as follows:

| Antiinflammatory Drug | Class | Dose mg/kg p.o. | % Inhibition of LTB$_4$ (ED$_{50}$) |
|---|---|---|---|
| Indomethacin | NSAID; CO inhibitor | 4 | 12 |
| Naproxen | | 4 | 0 |
| Diclofenac | | 10 | 0 |
| Ketoprofen | | 10 | 35 |
| Wy-50,295-A | LO-Inhibitor | 9 | (15) |
| BW540C | Mixed CO/LO inhibitor | | (30) |
| BW755C | | | (23) |
| Phenidone | | | (10) |

The compounds of the invention when tested in the reverse passive Arthus pleurisy assay gave the results shown in Table III.

TABLE III

| Compound of Example No. | Dose mg/kg, p.o. | % Inhibition LTB$_4$ Synthesis |
|---|---|---|
| 1 | 25 | 35 |
| 2 | 25 | 53 |
| 6 | 25 | 48 |
| 7 | 25 | 38 |
| 12 | 25 | 58 |
| 13 | 10 | 91 |
| 21 | 25 | 19 |

4. Inhibition of Bronchoconstriction in Guinea Pigs Induced by Exogenously Administered Antigen Male guinea pigs (Charles River, Wilmington, Mass.) were sensitized 3–4 weeks prior to antigen challenge by administration of 2 i.m. injections of ovalbumin, 1 into each hind limb (35 mg total). Sensitized animals (500–600 g) were fasted overnight prior to experimentation. Conscious animals were then dosed p.o. with drug or vehicle alone (0.5% Tween 80 in $H_2O$) at the indicated times prior to antigen challenge, or anesthetized animals were dosed i.v. with drug or vehicle alone (DMSO) 5 min prior to antigen challenge. Animals were anesthetized by urethane (2.8 g/kg i.p.). A carotid artery and jugular vein were cannulated to allow for the monitoring of blood pressure and the administration of drugs, respectively. The trachea was then cannulated and connected to a Harvard Apparatus rodent ventilator (S. Natick, Mass.). Spontaneous respiration was abolished by the administration of succinylcholine (2.5 mg/kg i.v.). The animals were then ventilated with room air at a rate of 65 breaths per min. Airway inflation pressure was measured using a Statham pressure transducer (Gould Instruments, Cleveland, Ohio) connected to the tracheal cannula via a side-arm and recorded on a Grass Instruments recorder (Quincy, Mass.). The tidal volume (approximately 10 cc/kg) was adjusted to give a baseline inflation pressure of 8–10 cm $H_2O$ at end inspiration. Animals were then allowed 20 min to stabilize.

Following the stabilization period, animals were given i.v. injections of pyrilamine (5 mg/kg), propranolol (0.1 mg/kg) and indomethacin (10 mg/kg) at 15, 10 and 5 min, respectively, prior to antigen challenge. This pretreatment results in an LT-dependent bronchoconstriction following antigen challenge, which was accomplished by i.v. administration of ovalbumin (10 mg/kg). Only one bronchoconstriction per animal was induced. End-inspiratory inflation pressure (in cm $H_2O$ over baseline) was measured at 5 min post-antigen challenge. A mean value and standard error for the % inhibition of control bronchoconstriction in each drug-treated group was then calculated. Data for invention compounds are presented in Table IV.

TABLE IV

| Compound of Example No. | Dose (mg/kg) | Administration Route | Bronchoconstriction % Inhibition |
|---|---|---|---|
| 1 | 20 | i.v. | 66 |
| 1 | 25 | p.o. | 25 |
| 1 | 25 | aerosol | 67 |
| 4 | 25 | aerosol | 51 |
| 13 | 20 | i.v. | 23 |
| 19 | 10 | i.v. | 21 |
| 21 | 10 | i.v. | 58 |
| 21 | 10 | p.o. | 34 |

5. Inhibition of Copper Ion Mediated Oxidation of Low Density Lipoprotein

In this in vitro assay, the inhibition of $Cu^{+2}$ mediated oxidation of rabbit or monkey LDL by an invention compound is determined spectrophotometrically. Oxidation of LDL results in the formation of LDL-diene which absorbs light at 532 nm. Inhibition of oxidation of LDL leads to a decrease in absorbance at 532 nm.

Rabbit or monkey LDL is prepared according to the procedures of Havel, Eder and Gragdon, "The Distribution and Chemical Composition of Ultracentrifugally Separated Lipoproteins in Human Serum,: *J. Clin. Invest.* 34, 1345–1353 (1955) and Parhtasarathy, Wieland and Steriberg, "A Role for Endothelial Cell Lipoxygenase in the Oxidative Modification of Low Density Lipoprotein," *Proc. Natl. Acad. Sci. USA* 86, 1046–1050 (1989). Test compound solutions are prepared by dissolving the invention compounds in ethanol at concentrations up to 248 μM. The medium used is Dulbecco's phosphate buffered saline containing 0.5 mg/ml bovine serum albumin. For standards, 0 to 10 μl of an aqueous solution of 1,1,3,3-tetraethoxypropane (1 μmol/ml $H_2O$) in 4.1 ml of medium is used.

Test compound solution (100 μl) is added to 4 ml of medium in incubation tubes. To each tube is added 10 μl of LDL solution and 25 μl of aqueous copper sulfate solution (1.32 mg/ml $H_2O$). The tubes are incubated at 37° C. for 90 minutes and the oxidation reaction quenched by addition of 1 ml of thiobarbituric acid solution (0.67% in 50% acetic acid). The tubes are heated at 90° C. for 1 hour, then chilled in an ice bath and the chromophore extracted into 2 ml of n-butanol. Absorbence is read at 532 nm and the results are reported as nmols of malondialdehyde equivalents.

Significant differences ($p<0.05$) are determined by the Dunnett T-test or by the Student-Newman-Keuls Test for significant differences between means. The assay is conducted using several concentrations [I] of the inhibitor test compounds. The LDL solution concentrations at different experiments were either 1.5 mg/ml, 2.5 mg/ml or 10.3 mg/ml. The $IC_{50}$ is determined by non-linear regression, plotting log [I] vs. % inhibition. (Reference: K. Yagi, Biochemical Medicine 15, 212–216 (1976)). The results obtained with invention compounds are shown in Table V.

TABLE V

| Example No. | $IC_{50}$ (μM) |
|---|---|
| 1 | 0.69 |
| 4 | 1.3 |
| 10 | 0.18 |
| 13 | 0.82 |

Pharmaceutical Composition

When the compounds of the invention are employed in the treatment of allergic airway disorders, inflammation, or atherosclerosis, they can be formulated into oral dosage forms such as tablets, capsules and the like. The compound can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be administered parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of treating inhibiting atherosclerotic plaque formation in a mammal in need thereof which comprises administration of a therapeutically effective amount of a compound having the formula:

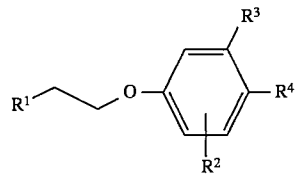

wherein: $R^2$ is hydrogen, halogen or $C_1$–Calkyl;
one of $R^3$ and $R^4$ is H and the other is

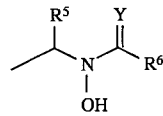

Y of O or S;
$R^5$ is hydrogen or methyl
$R^6$ is $-NH_2$, $-CH_3$ or $-OCH_3$;
and $R^1$ is

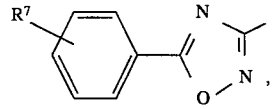

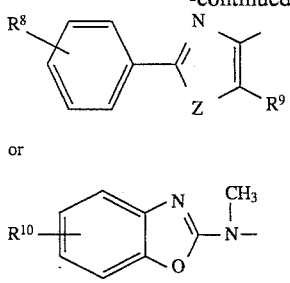

or

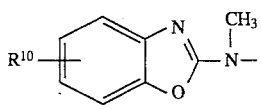

wherein $R^7$, $R^8$ and $R^{10}$ are independently halogen, trifluoromethyl, alkyl, alkoxy, methanesulfonyl or trifluoromethanesulfonyl; $R^9$ is hydrogen or methyl; and Z is O or S, or a pharmaceutically acceptable salt thereof.

2. A method of treatment according to claim 1 wherein the compound used is selected from:

1-[4-[2-[2-(3,5-di-tert-butyl-4-hydroxy-phenyl)-5-methyl-oxazol-4-yl]-ethoxy]-benzyl]-1-hydroxy-urea;

1-hydroxy-1-[4-[2-(2-phenyl-thiazol-4-yl)-ethoxy]-benzyl]-urea;

1-hydroxy-1-[4-[2-(2-phenyl-thiazol-4-yl)-ethoxy]-benzyl]-thiourea;

1-hydroxy-1-[4-[2-[2-(4-trifluoromethyl-phenyl)-thiazol-4-yl]-ethoxy]benzyl]-urea;

1-hydroxy-1-[3-[2-[2-(4-trifluoromethyl-phenyl)-thiazol-4-yl]-ethoxy]-benzyl-urea;

1-[4-[2-(benzoxazol-2-yl)-methyl-amino]-ethoxy]-benzyl]-1-hydroxy-urea;

N-[4-[2-(benzoxazol-2-yl)-methyl-amino]-ethoxy]-benzyl-N-hydroxy-acetamide;

[[4-[2-(benzoxazol-2-yl-methyl-amino)-ethoxy]-benzyl]-methyl]-carbamic acid methyl ester;

and 1-hydroxy-1-[4-[2-(5-phenyl-[1,2,4]-oxadiazol-3-yl)-ethoxy]-benzyl]-urea or a pharmaceutically acceptable salt thereof.

* * * * *